(12) United States Patent
Boulbitch

(10) Patent No.: US 8,884,219 B2
(45) Date of Patent: Nov. 11, 2014

(54) DIFFERENTIAL MOBILITY SPECTROMETER WITH ASYMMETRICALLY OSCILLATING DRIVING ELECTRICAL FIELD

(75) Inventor: Alexei Boulbitch, Igel (DE)

(73) Assignee: IEE International Electronics & Engineering S.A., Luxembourg (LU)

( * ) Notice: Subject to any disclaimer, the term of this patent is extended or adjusted under 35 U.S.C. 154(b) by 605 days.

(21) Appl. No.: 12/988,768

(22) PCT Filed: Apr. 17, 2009

(86) PCT No.: PCT/EP2009/054622
§ 371 (c)(1),
(2), (4) Date: Jan. 17, 2011

(87) PCT Pub. No.: WO2009/130172
PCT Pub. Date: Oct. 29, 2009

(65) Prior Publication Data
US 2011/0260050 A1    Oct. 27, 2011

(30) Foreign Application Priority Data

Apr. 22, 2008 (EP) ................................. 08154962

(51) Int. Cl.
*H01J 49/42* (2006.01)
*G01N 27/62* (2006.01)

(52) U.S. Cl.
CPC .............. *H01J 49/42* (2013.01); *G01N 27/622* (2013.01)
USPC ............................ 250/287; 250/281; 250/282

(58) Field of Classification Search
USPC ........................... 250/281, 282, 287, 292, 293
See application file for complete search history.

(56) References Cited

U.S. PATENT DOCUMENTS 6,124,592 A * 9/2000 Spangler ....................... 250/287
6,512,224 B1 * 1/2003 Miller et al. .................. 250/286

(Continued)

FOREIGN PATENT DOCUMENTS

WO    97/47025       12/1997
WO    2004030129     4/2004

(Continued)

OTHER PUBLICATIONS

International Search Report; PCT/EP2009/054622; Jun. 16, 2009.

(Continued)

*Primary Examiner* — Brooke Purinton
(74) *Attorney, Agent, or Firm* — Cantor Colburn LLP

(57) ABSTRACT

A method of operating a differential mobility spectrometer includes an ionization chamber, a filter channel and a detection region. In the ionization chamber, analyte ions are produced from a sample, the so-obtained ions are then subjected in the filter channel to a time-varying electric field. The time-varying electric field has a longitudinal field component drawing the analyte ions from the ionization chamber through the filter channel into the detection region and a transversal field component, which is the superposition of an asymmetrically oscillating transversal field causing the analyte ions to move to and fro in transversal direction and a compensation field for selecting a species of analyte ions by substantially canceling the average transversal velocity of the selected species. Analyte ions of the selected species having passed through the filter channel are collected in the detection region and a detection signal responsive to the number of analyte ions collected is generated as a function of the compensating field. The longitudinal field component oscillates in longitudinal direction in such a way that it imparts to the analyte ions on average a non-zero longitudinal velocity in direction of the detection region while it causes them, on a shorter time scale, to move to and fro in longitudinal direction in the filter channel.

20 Claims, 4 Drawing Sheets

(56) References Cited

U.S. PATENT DOCUMENTS

| | | | |
|---|---|---|---|
| 7,449,683 B2* | 11/2008 | Shvartsburg et al. | 250/287 |
| 2003/0038235 A1* | 2/2003 | Guevremont et al. | 250/287 |
| 2003/0146377 A1* | 8/2003 | Miller et al. | 250/286 |
| 2005/0145789 A1* | 7/2005 | Miller et al. | 250/290 |
| 2005/0230615 A1* | 10/2005 | Furutani et al. | 250/287 |
| 2007/0084999 A1* | 4/2007 | Miller et al. | 250/288 |
| 2008/0191132 A1* | 8/2008 | Boyle et al. | 250/287 |
| 2008/0210861 A1* | 9/2008 | Wu et al. | 250/287 |
| 2009/0189064 A1* | 7/2009 | Miller et al. | 250/282 |
| 2009/0239252 A1* | 9/2009 | Trevejo et al. | 435/29 |
| 2010/0282961 A1* | 11/2010 | Miller et al. | 250/282 |
| 2011/0036973 A1* | 2/2011 | Alonso et al. | 250/282 |

FOREIGN PATENT DOCUMENTS

| | | |
|---|---|---|
| WO | 2006013396 | 2/2006 |
| WO | 2007034239 | 3/2007 |

OTHER PUBLICATIONS

A. Kudryavtsev, et al; "Ion Focusing in an Ion Mobility Increment Spectrometer (IMIS) with Non-Uniform Electric Fields: Fundamental Considerations" International Journal of Mass Spectrometry 4, pp. 117-120, Jan. 2001.

E.V. Krylov, et al.; "Differential mobility spectrometer: Model of operation"; International Journal of Mass Spectrometry 266 (2007), pp. 76-85.

Erkinjon G. Nazarov, et al; "Miniature Differential Mobility Spectrometry Using Atmospheric Pressure Photoionization"; Analytical Chemistry, vol. 78, No. 13, Jul. 1, 2006, pags 4553-4563.

G.A. Eiceman, et al.; "Separation of Ions from Explosives in Differential Mobility Spectrometry by Vapor-Modified Drift Gas"; Analytical Chemistry, vol. 76, No. 17, Sep. 1, 2004, pp. 4937-4944.

H. Borsdorf, et al.; "Atmospheric-pressure ionization studies and field dependence of ion mobilities of isomeric hydrocarbons using a miniature differential mobility spectrometer"; Analytica Chimica Acta 575 (2006); pp. 76-88.

Helko Borsdorf, et al.; "Ion Mobility Spectrometry: Principals and Applications"; Applied Spectroscopy Reviews, 41, (2006); pp. 323-375.

I.A. Buryakov; "Qualitative analysis of trace constituents by ion mobility increment spectrometer"; Talanta 61 (2003); pp. 369-375.

I.A. Buryakov, et al.; "A new method of separation of multi-atomic ions by mobility at atmospheric pressure using a high-frequency amplitude-asymmetric strong electric field"; International Journal of Mass Spectrometry and Ion Processes 128 (1993), pp. 143-148.

J.R. Millard, et al.; "Mechanisms of Pulsed UV Laser Ionization of Molecules Adsorbed to Thin Metal Films"; J. Phys. Chem. 1987, 91, pp. 4323-4329.

N. Krylova, et al.; "Effect of Moisture on the Field Dependence of Mobility for Gas-Phase Ions of Organophosphorus Compounds at Atmospheric Pressure with Field Asymmetric Ion Mobility Spectrometry"; The Journal of Physical Chemistry; 2003, 107, pp. 3648-3654.

* cited by examiner

DIFFERENTIAL MOBILITY SPECTROMETER WITH ASYMMETRICALLY OSCILLATING DRIVING ELECTRICAL FIELD

TECHNICAL FIELD

The present invention relates to devices for analysis of components of gases. More precisely, it relates to an improvement of devices known as Micro Differential Mobility Spectrometers (micro-DMS). These devices operate by ionizing the gas composition to be examined and separating the various ionized gas components by a mechanism that makes use of the different dependencies of the ion mobilities of these components upon the electric field.

BACKGROUND ART

Gas analysis based on field-dependent ion mobility is a powerful tool in a number of applications of a primary importance, e.g. public protection against terrorism as well as protection of military staff. This is because differential ion mobility spectrometers are capable of detecting traces of explosives and poison agents present in ambient air. Another possible application of such spectrometers is remote detection of illegal drugs.

Recently, new applications of broad industrial and public interest have emerged from scientific developments, e.g. in medicine for the purposes of fast non-invasive diagnostics, in food industry for early detection of food spoilage, as well as for testing of status of production processes in many industrial branches. Further, security and health of people in their everyday life may be improved by air control in enterprises, in living rooms, in cars, in streets with heavy traffic and so on. Such public applications necessitate millions of individual spectrometers and can only become realistic if such devices can be manufactured at low costs. An important step was taken with the development of micro-machined differential mobility spectrometers ("A MEMS fabricated FAIMS device", B. Boyle, Contribution at the Conference ISIMS 2007. Mikkeli, Finland; 2007, see also http://www.owlstonenanotech.com).

The parameters of differential mobility spectrometers, e.g. their dimensions, operating voltages, operating frequencies are restricted by several conditions imposed by the filtering principle used. In addition, there are technical requirements (e.g. the miniaturization) that limit the freedom to choose the values of these parameters. This will hereinafter be elaborated in more detail.

The phenomenon of field-dependent ion mobilities was described by Mason and McDaniel in "The Mobility and Diffusion of Ions in Gases" (Wiley, New York; 1973). In the early 1980s, it was Gorshkov, who was the first to disclose a method making use of this differential mobility for spectrometry (see SU 966583), and later, in the 1990s, Buryakov et al. who presented practical implementations of the Differential Mobility Spectrometry (DMS) technique (see Soviet Technical Physics Letters 1991, vol. 17, no. 6, p. 446-447, SU 1412447, RU 2150157). Further developments of the technique were made, for instance, by Guevremont (see WO 2001/69219 and US 2005/161597 A1) and Miller (US 2005/051719 A1).

It should be borne in mind that in the literature several terms and abbreviations are used to refer to this method, e.g. Field Asymmetric Ion Mobility Spectrometry (FAIMS), Ion Mobility Increment Spectrometry (IMIS), Ion Non-Linear Drift Spectrometry, Ion Drift Spectrometry, High-Fields Asymmetric Waveform Ion Mobility Spectrometry, Field Asymmetric Ion Mobility Spectrometry, Radio-Frequency-Based Ion-Mobility Analysis, Radio Frequency Ion Mobility Spectrometry (RF-IMS) and Field Ion Spectrometry. Herein, we will use the term "Differential Mobility Spectrometry" and its abbreviation "DMS".

A DMS device typically comprises an ionization chamber, a separation region (also referred to as "filter" or "filter chamber") and an analysis (or detection) chamber arranged in series. According to the inventions disclosed in the publications referenced above, the carrier gas (typically, but not limited to, ambient air at atmospheric pressure) containing some additives in the gaseous state (hereafter referred to as "analytes") is delivered into the ionization chamber by a gas flow. In the ionization chamber, the analytes are ionized and the mixture of ions and carrier gas is further delivered into the separation region by the gas flow. The separation region contains at least two electrodes (referred to as the "separation electrodes") disposed in such a way that the gas flow carries the ions through the space between these electrodes. A high-frequency electric voltage is applied to the separation electrodes in such a way that the resulting electric field forces the ions to move transversely to the direction of the gas flow. This transversal motion is superimposed on the initial motion through the separation region caused by the gas flow. The voltage across the separation electrodes, denoted $U_s$, is referred to herein as "separating voltage", while the corresponding electric field, denoted $E_s$, is referred to as the "separating" or "transversal" field. The voltage is chosen "asymmetrically". That is, each period of the voltage consists of at least two pulses of opposite polarity; the pulses are said to have "forward" or "backward" polarities, respectively. The at least one forward pulse is chosen to be stronger (to have higher amplitude) than the at least one backward pulse, but the duration of the forward pulse(s) is chosen to be shorter than that of the backward pulse(s), so that for the electric field the equality $\int_0^{T_s} E_s(t)dt=0$ is valid. Here, $E_s(t)$ is the transversal electric field strength, $T_s$ is the period of its temporal variation and t is time. In general, the velocity (V) of the ions in the carrier gas subjected to an electric field E is expressed as $V=KE$, where K is the mobility, expressed as $K=K_0[1+\alpha(E)]$. Here, $K_0$ is the ion mobility in a small electric field, while the factor $\alpha=\alpha(E)$ (referred to as the "mobility increment") accounts for the dependence of the mobility upon the electric field and represents in general a non-linear function of $E^2$. Due to the time-dependency imposed on the transversal electric field, the average velocity gained by the ion during a period of the field is $\langle V \rangle =K_0 T_s^{-1}\int_0^{T_s}\alpha[E_s(t)]\times E_s(t)dt$. In the general case, $\langle V \rangle$ is non-zero and essentially depends upon the mobility increment. Thus, the applied transversal electric field results in the ions of the analytes moving towards one of the separating electrodes. As soon as they hit the electrodes, the ions reconstitute. The above publications teach that the high-frequency transversal field can be supplemented by a slowly varying component, $E_c(t)$, (referred to as the "compensating field") so that the transversal field has the form $E(t)=E_s(t)-E_c$. Slowly scanning the parameter $E_c$ reveals some values of $E_c$ at which a certain sort of analytes has zero average transversal velocity increment during a period of the transversal electric field: $\langle V \rangle \approx \int_0^{T_s}\alpha[E_s(t)-E_c]\times E_s(t)dt - E_c\int_0^{T_s}\alpha[E_s(t)-E_c]dt=0$. Those ions for which this relation is valid in average do not move, again in average, towards one of the separating electrodes. As a consequence, they pass through the separation region and enter the analysis chamber.

In conventional macroscopic gas-flow-driven DMS devices, the analysis chamber contains at least two electrodes connected to a measuring device through an amplifier. This enables one to register small ionic currents as the ions, which have passed through the separation region, hit one of these electrodes. Thus, the described set up enables one to register a current signal, J, as the function of the compensating electric field, $E_c(t)$. Plotting the current signal J against $E_c(t)$ reveals a characteristic set of peaks. The peak maxima are located at those $E_c$ values at which (at least) one species of analytes passes through the filter. At least some of the peaks are separated from one another. Such $J=J(E_c)$ dependence is referred to as a DMS spectrum. The DMS spectrum enables one to identify the analytes based on the differences in their mobility increments. This is the main distinction of the DMS method with respect to other gas analysis methods, such as e.g. Ion Mobility Spectrometry, Aspiration Ion Mobility Spectrometry and the Time-of-Flight Mass Spectrometry, which rely upon the mobility $K_0$ itself (instead of its increment) to distinguish between different species of analytes. Ideally, each of the peaks of a DMS spectrum corresponds to one and only one analyte species. In practice, however, several analytes may have similar mobility increments and thus give rise to overlapping or superimposed peaks. In certain cases, peaks caused by different analytes may even be indistinguishable from one another. The reasons for this are discussed in details below.

In the patent documents and scientific papers cited above, the carrier gas charged with analytes is delivered into the device by a gas flow (provided, for instance, with a mechanical pump). In contrast to that, patent application WO 2001/035441 (Miller and Zahn) teaches to use an electric field for delivering the ions into the separation region.

The DMS filters disclosed in the contributions cited above are all of macroscopic size. Typically, they have a length of about 10 cm and a lateral dimension of a few centimeters. Patent applications WO 2007/034239 (Alonso et. al.), WO 2006/046077, WO 2006/013396 and WO 2007041551 (Boyle et. al.) disclose micro-machined DMS, in which the analyte ions are caused to drift by an electric field (longitudinal or "drive" field) oriented in direction of the gas flow and generated by a special pair of deviating electrodes. These patent applications also disclose methods of fabrication of such devices. The microscopic (sub-millimeter) size of the device is favorable, since it enables one to apply considerably smaller voltage across the separating electrodes and at the same time keep the high value of the electric field strength that is intrinsically required for DMS. This is achieved due to a strong reduction of the inter-electrode distance of the device. Further, the sub-millimeter length (i.e. the device dimension along the direction of the drift of ions) enables one to apply a relatively small voltage also in this direction.

The above-mentioned patent applications disclose devices operating with a static (that is, time-independent) longitudinal electric field. WO 2006/013396 and WO 2007/034239 also mention that the longitudinal electric field is preferably a static electric field but a time-varying drive field can be employed. The patents however, give no details on possible variations of the longitudinal electric field.

One aspect of the present invention relates to light-induced ionization of analytes. Therefore, publications related to this subject are briefly reviewed below.

At present, in about 90% of the cases, ionization in DMS devices is provided by β-radioactive sources (such as $^{63}$Ni) due to low and easy service requirements, low price and high stability of such sources. Application of β-radioactive components does not usually create a major concern in military or police applications. Mass market introduction of such β-source-based devices is, however, hindered by strict law requirements on the one hand and public prejudice against any sort of radioactivity on the other hand.

A further well established method of ionization uses the so-called electro-spray effect. Due to its intrinsic properties this method leads to a fast contamination of the devices and may be mortal for micro-devices.

The third main option for ionizing analytes is UV-light ionization. A number of aspects of UV ionization in DMS applications have already been disclosed in the past. In patent application WO 01/69219, Guevremont et al. disclosed the idea of a laser-based ionization source combined with the DMS device. The main idea of the document is to use the so-called matrix-assisted laser decomposition ionization together with DMS. In matrix-assisted laser decomposition ionization (MALDI), the solid or liquid sample is mixed with a material called a "matrix" and the combination is dried on a metal support electrode. A laser beam is directed onto this surface and ions of the analyte compound are formed. In WO 01/69219 it is proposed to use this method with a DMS of cylindrical configuration and to provide the DMS with a device able to partially remove the inner electrode on which the samples are deposited from its position, to bring it back as well as to rotate it along its axis. This document also discloses a special orifice (sample introduction port) through which the matrix/sample mixture may be applied to the inner electrode upon a partial removal of the latter. In US 2005/0161597, Guevremont et al. disclosed a set of combinations of a DMS device with one or several lasers, in which the ionization process takes place outside the DMS filter and the resulting plasma is brought into the separation region afterwards.

In the papers Borsdorf H, et al., Analytica Chimica Acta 575, 76 (2006) and Nazarov E. G., et. al. Analytical Chemistry 78, 4553 (2006), the application of krypton discharge lamps with DMS for photoionization of hydrocarbons has been described.

In addition to papers and patent documents disclosing the use of optical ionization tools for the DMS applications, a number of publications disclosed the use of UV-light ionization along with other ion-separating devices such as the Ion Mobility Spectrometer, the Time-of-Flight Mass Spectrometer etc. Those skilled in the art readily understand that normally the means applicable to those devices can be also used with DMS.

U.S. Pat. No. 4,398,152 to Leveson discloses a construction of a gas lamp in which plasma is generated by the radiofrequency AC voltage. The UV light from the lamp is intended to ionize gases in ion mobility spectrometers. Patent application WO 93/22033 discloses a construction of an Ion Mobility Spectrometer with a flash lamp as the ionization source. In this case, the flash lamp irradiates the mixture of air and analyte within the Ion Mobility Spectrometer, which results in ionization of the mixture. The resulting plasma is then delivered into the filter region. U.S. Pat. No. 5,968,837 to Adler et al. discloses to enhance photoionization by addition of dopants. U.S. Pat. No. 5,541,519 to Stearns and Wentworth discloses the combination of a flash lamp and an Ion Mobility Spectrometer. The gas to be analyzed is mixed with a rare gas in the drift chamber of the Ion Mobility Spectrometer and is subjected to a high voltage from the discharge electrodes. The following discharge causes UV irradiation ionizing the analyte gas. In U.S. Pat. No. 5,808,299 to Syage, photoionization has been proposed as a method of ionization of gases analyzed by a Mass-Spectrometer, while in EP 1 726 946 and US 2005/138594 of the same author, a combination of a discharge ionization device with a photoionization device has been proposed for increasing the sensitivity of an Ion Mobility Spectrometer. In U.S. Pat. No. 5,338,931 to G. E. Spangler and J. E. Roehl, flash lamp-based ionization for Ion Mobility Spectrometer has been disclosed. A gas sample is introduced via a carrier gas into a ionization chamber, which is part of the spectrometer cell. Ionizable molecules contained in the injected gas sample are ionized by ultraviolet light emitted from a flash lamp. In WO 2001/019501 to W. Yang and P. C. His, a photoionization device for Ion Mobility Spectrometry has been proposed, which includes either multiple UV lamps, each having a specific energy level for discriminating between potential constituents of the gas sample, or a single multiple-energy level UV lamp (does not exist yet) with different light bandwidth window zones and a zone selector.

UV photoionization was also proposed for application in time-of-flight mass spectrometer. In this context, it was shown that the use of an adsorbing surface may increase the number of the ionized molecules over three orders of magnitude (Millard JR, et. al., J. Phys. Chem. 91, 4323 (1987); WO 2001/019501 A1).

In WO 2006/013396 to Boyle et. al. it is mentioned that UV ionization sources may be used together with micro-machined DMS devices. No details of their use, however, have been disclosed.

Finally, an ionization device for Ion Mobility Spectroscopy based on X-rays has been recently reported by Heller, W. et al. in "Ion mobility spectrometry with X-ray tubes as ionization device", Contribution at the International Symposium on Ion Mobility Spectrometry ISIMS 2007, Mikkeli, Finland; Jul. 22-27, 2007.

The nature of the DMS method imposes certain limitations on construction of DMS devices. For example, the distance between the separating electrodes (hereinafter referred to as distance d) cannot be chosen arbitrarily. First, the transversal electric field strength must reach a certain value in order to make the field-dependence of the mobility increment a measurable effect. From typical results found in literature (I. A. Buryakov et al., IJMS 128, 143 (1993); I. A. Buryakov, Talanta 61, 369 (2003); I. A. Buryakov, ZhTF 74, 15 (2004) and I. A. Buryakov, ZhTF 72, 109 (2002); G. A. Eiceman et al., Anal. Chem. 76, 4937 (2004); N. Krylova et al., J. Phys. Chem. A107, 3648 (2003) and Krylov, E. V. et. al. IJMS 266, 76 (2007)) one can conclude that the amplitude of the electric field strength $E_{s,req}$ required for these purposes should be in the range $10^4$-$10^5$ V/cm. Thus, for a given inter-electrode voltage (between the separating electrodes), the inter-electrode distance d is subject to the inequality:

$$d \leq U_s/E_{s,req} \quad (-1-)$$

Second, in the inter-electrode region of the separation region, the ions of analytes follow a zigzag course. This requires that the inter-electrode distance be much larger than the amplitude of the zigzag motion, which yields the condition:

$$(K_0 U_s t_1)^{1/2} << d \quad (-2-)$$

where $t_1$ is the duration of the forward phase of the period. Conditions (-1-) and (-2-) yield:

$$U_s > K_0 t_1 E_{s,req}^2 \quad (-3-)$$

(-3-) defines a lower bound the separating voltage. In addition, due to technical requirements, the separating voltage should be as low as possible. In order to enable the use of comparably simple electronics and keep energy consumption and operational costs within reasonable limits, one may impose:

$$U_s \leq U_{up} = 100 \text{ V}$$

This condition is not determined by any intrinsic physics of the phenomenon and can be considered as a "soft" requirement, in the sense that it may be varied, if necessary within the order of magnitude.

These limitations will now be estimated for the example of the Lonestar™ chemical detector produced by Owlstone Ltd. (http://www.owlstonenanotech.com/site.php). It will be assumed that the transversal electric field strength $E_t \sim 10^4$ V/cm, (where the symbol "~" means "equal by their orders of magnitude") and that $t_1 \sim T_s$, where $T_s$ is the period of the separation field. In this example, the period $T_s$ is $3 \times 10^{-8}$ s (presentation at the ISIMS 2007, Mikkeli, Finland, Jul. 22-25, 2007). A typical estimate for the ion mobility of explosives is $K_0 \approx 1$ cm$^2$/(V×s) (cf. I. A. Buryakov, ZhTF 72, 109 (2002) and A. Kudryavtsev et. al. IJIMS 4, 117 (2001)). Condition (-3-) then yields $U_s > 3.8$ V. If we assume that for technical reasons, there is an upper bound of 10 V, we find that the inter-electrode distance d may be selected in the range from 6 μm to 10 μm. Increasing the upper limit of the voltage makes the acceptable interval wider. For instance, with $U_s \approx 100$ V one finds 20 μm<d<100 μm.

The next restriction is imposed on the period $T_s$ of the oscillations of the separation field. It is related to the fact that for the filtering to be efficient the ions must make a lot of zigzag steps during the time $T_f$ of their flight through the filter. If the ions are driven through the filter by a driving electric field (denoted $E_d$) caused by a voltage $U_d$, the time of flight is expressed as $T_f = L^2/K_0 U_d$, where the length L is the dimension of the filter in the direction of flight. This yields the condition $$\frac{L^2}{K_0 U_d T_s} \gg 1 \quad (-4-)$$

For instance, in a device with a length L=200 μm, a driving voltage of 40 V and an operating frequency $T_s^{-1}$=10 MHz and assuming a typical ion mobility $K_0 \sim 1$ cm$^2$/(V×s), one finds $L^2/(K_0 U_d T_s) \sim 100$, which agrees with requirement (-4-).

In case of a static driving field, its strength must be smaller than the electric breakdown value $E_b$ (~$3 \times 10^4$ V/cm in dry air at atmospheric pressure), and the corresponding driving voltage $U_d$ should be below a technically required upper value $U_{up}$. This yields the conditions:

$$U_d < E_b L \text{ and } U_d \leq U_{up} \quad (-5-)$$

For a device with L=200 μm one obtains, therefore, $U_d$<600 V. Operating at the voltages close to this limit would bear the risk of electric breakdown but, in practice, the voltage is typically below the above-mentioned "soft" limit $U_{up}$.

A lower limit for the driving voltage $U_d$ can be derived from device-related, practical limitations. The signal of the DMS device can be registered in different ways. For example, a mass spectrometer could be built in series with the DMS separation chamber and play the role of the detection region. However, the most simple and practical method is to register the ionic current directly in the detection region using an electrometer or comparable instrument. In conventional DMS devices, this is usually done by placing of at least one pair of electrodes into the detection region. In an electric-field-driven DMS device, one or both of the deflection electrodes may play the role of such detection electrodes and, in this case, only one detection electrode is situated inside the detection region. In both cases, the detected current caused by the analyte ions that reach the detection region can be expressed as:

$$J = \frac{qN_{an}^{(i)}K_0A}{L}U_d. \qquad (\text{-6-})$$

Here J is the ionic current measured in the detection circuit, q is the electric charge carried by the ions, A is the area of the cross-section of the separation chamber normal to the average ion trajectory and $N_{an}^{(i)}$ is the density (in particles per unit volume) of the analyte ions delivered to the detection electrode(s). The latter considerably differs from the density $N_{an}$ of analyte molecules that enter the ionization chamber: $N_{an}^{(i)}=\beta N_{an}$. Factor $\beta$ accounts for the efficiency of the ionization as well as for numerous losses of ions on their way to the detection region. It depends, therefore, upon the ionization method, the composition of the carrier gas and the geometries of the ionization and separation chambers. It may also equivocally depend upon the intensity of the electric field in the separation chamber and characteristics of the waveform, since these parameters influence the losses. According to equation (-6-), the minimal measurable value of the electric current $J_{min}$—corresponding to the noise level of the electrometer—determines the minimal acceptable value for the driving voltage $U_d^{(min)}$. For the ionic current to be well distinguishable from noise, the driving voltage must provide a required signal-to-noise ratio R (e.g. at least 10). This yields the limitation:

$$U_d \geq R \times \frac{LJ_{min}}{qN_{an}K_0A\beta} \qquad (\text{-7-})$$

Assuming, as an example, that the required signal-to-noise ratio is R=10, $\beta\sim0.001$, L=200 mm, there are about 50 filter channels disposed in parallel having each the lateral dimensions of 100 µm×400 µm, the noise level is $J_{min}\sim10^{-2}$ pA, $N_{an}\sim10^6$ cm$^{-3}$, $K_0\sim1$ cm$^2$V$^{-1}$s$^{-1}$ and q=1.6×10$^{-19}$ C per ion, on finds $U_d$>100 V. The ionic current, to which this driving voltage leads according to (-6-), amounts to J~0.1 pA, which is a small but still measurable value exceeding the noise level, $J_{min}$. The minimal acceptable value for the driving voltage thus depends upon the design of the device and the properties of the analyte through its mobility, charge and density. In this example, a very low analyte concentration was used, which corresponds to the detection limit of ~10$^{-12}$ g/l of tetraethylamine (I. A. Buryakov, E. V. Krylov et al. Zh. Analit. Khim. 1993; 48 (1): 156-65). If the device is designed for higher analyte concentrations or/and with a better efficiency, the necessary driving voltage could be lower.

Another requirement imposed on device parameters is related to the resolution of the DMS device. The arguments given below show that a conventional device is unable to distinguish ions with mobility increment $\alpha=\alpha^{(0)}$ from ions with $\alpha=\alpha^{(0)}\pm\Delta\alpha$, with $\Delta\alpha$ in a certain interval. For the results provided by the device to be reliable, the inequality $\alpha^{(0)}>\Delta\alpha$ must be fulfilled. Furthermore, the smaller is the ratio $r=\Delta\alpha/\alpha^{(0)}$, the higher is the resolution of the device.

Assume that an electric field $E=E_s(t)-E_c^{(0)}$ is applied across the separating electrodes, and for a certain compensating field $E_c^{(0)}$, the ions possessing the mobility increment $\alpha=\alpha^{(0)}$ are not deviated to the separating electrodes, i.e. pass through the filter and are detected. Ions with $\alpha=\alpha^{(0)}(E)+\Delta\alpha$ (E) (different from $\alpha^{(0)}$), however, move towards the one of the separating electrodes with the average velocity $\langle V\rangle\approx K_0\rangle\Delta\alpha[E(t)]\times E(t)\rangle\neq 0$ and will eventually reach that electrode, provided that $\langle\Delta\alpha[E_s(t)]\times E_s(t)\rangle K_0T_f\geq d$, where the time of flight $T_f$ is defined as $T_f=L/V_d$ in the general case or $T_f=L^2/K_0U_d$ in case the ion flow is generated by a driving electric field. Here $V_d$ and $U_d$ are the longitudinal velocity and the driving voltage across the deviating electrodes, respectively. Ions with $\alpha\neq\alpha^{(0)}$, but $\langle\Delta\alpha[E_s(t)]\times E_s(t)\rangle\times K_0T_f<d$ will pass through the separation region and will be registered in the analyzing chamber indistinguishable from the ions with $\alpha=\alpha^{(0)}$.

Example: Typically the mobility increment manifests itself at E/N>10 Td, where N is the air density (in particles per cm$^3$) and unit Td (Townsend) is defined by: 1 Td=10$^{-17}$ V×cm$^2$. One usually extracts the dependence of the mobility increment, $\alpha=\alpha(E/N)$, upon the reduced electric field, E/N, from experimental data in a form of a polynomial $\alpha(E/N)=\alpha_2E^2/N^2+\alpha_4E^4/N^4+\ldots$, where $\alpha_2$ and $\alpha_4$ are coefficients (see, for example, Buryakov ZhTF 2004; 74(8):15-20; Buryakov Talanta 2003; 61(3):369-375 and Krylova et. al. J. Phys. Chem. A 2003; 107(19):3648-3654). If the reduced the electric field strength E/N obeys the relation E/N<<$(\alpha_2/\alpha_4)^{1/2}$, the one-parametric representation $\alpha(E/N)\approx\alpha_2E^2/N^2$ accurately describes the mobility increment. The above papers (as well as other publications) report the values of $\alpha_2$ and $\alpha_4$ for various substances of interest in the range of $\alpha_2\approx10^{-6}$ to $10^{-7}$ Td$^{-2}$ and $\alpha_4\approx10^{-10}$ to $10^{-11}$ Td$^{-4}$, respectively. This yields a relatively broad interval of 10<E/N<100 Td, in which the mobility increment is manifested while the one-parametric representation is valid. Assuming further that the separating field is represented as follows: $E_s(t)=U_sf(t)/d-E_c$, where $U_s$ is the amplitude of the voltage across the separating electrodes and f(t) is the so-called waveform, and where $E_c$ is the compensating field. Assume that there is a sort of ions which have as mobility increment $\alpha_2=\alpha_2^{(0)}$ and for which the average transversal velocity is zero for a certain value of $E_c$. Then all the ions with $\alpha_2=\alpha_2^{(0)}+\Delta\alpha_2$ such that $K_0E_s^3\langle f^3\rangle\Delta\alpha_2T_f/N^2<d-K_0U_st_1/d$ will be registered in the detection chamber. Here, $\langle f^3\rangle=T_s^{-1}\int_0^{T_s}f^3(t)dt$ and $t_1$ is the duration of the positive pulse. One finds the condition:

$$r=\frac{d^2N^2U_d(d^2-U_sK_0t_1)}{L^2U_s^3\langle f^3\rangle\alpha_2^{(0)}}\ll 1 \qquad (\text{-8-})$$

which again involves the spatial dimensions of the device. If the inequality (-2-) is fulfilled, the condition (-8-) can be simplified and takes the form:

$$r=\frac{d^4N^2U_d}{L^2U_s^3\langle f^3\rangle\alpha_2^{(0)}}\ll 1 \qquad (\text{-9-})$$

Condition (-9-) can be useful if the parameters of the device are close to the boundary defined by (-2-). To demonstrate this condition we make use of the voltages of operation of the Owlstone device $U_d=U_s=40$ V, its length L=200 µm, its interelectrode distance d=100 µm. We further take the air density at normal conditions $N\approx10^{19}$ cm$^{-3}$ and use the typical values of the parameter) $\alpha_2^{(0)}\approx10^{-7}-10^{-5}$ Td$^{-2}$ (I. A. Buryakov, Talanta 61, 369 (2003) and ZhTF 72, 109 (2002), N. Krylova et al., J. Phys. Chem. A107, 3648 (2003)). In case of rectangular pulses described as f(t)=1 for 0<t≤$t_1$ and f(t)=$-T_s/(t_1-T_s)$ for $t_1$<t≤$T_s$, at a repetition rate of 10 MHz, one finds $T_s$=0.1 µs. Assuming $t_1$=0.03 µs one finds $\langle f^3\rangle\approx0.2$. This yields r≈100–10>>1. The estimate shows that such a device is unable to give reliable results. Even a 10-fold increase in filter length up to L=2 mm, yields the resolution factor close to unity r≈1−0.1, which still results in a risky regime of operation.

All parameters discussed above are important. However, the parameter r (-8-) has primary importance since its value determines whether the spectrum measured by the device has any physical sense at all. The above analysis demonstrates that there is limited freedom for varying the parameters of a micro-DMS device in order to decrease r (e.g. by variation of voltages or the inter-electrode distance d). The device length is not restricted by any condition other than (-8-) and therefore, it would be possible to increase the length, which would result in a decrease of r proportional to $L^{-2}$. Considerable increase in L however, imposes problems for the micro-machining of the device.

TECHNICAL PROBLEM

It is an object of the present invention to provide a differential mobility spectrometer with increased resolution with respect to conventional such devices having similar size. This object is achieved by applying the method according to claim 1, or a spectrometer according to claim 11.

GENERAL DESCRIPTION OF THE INVENTION

The present invention concerns a method of operating a differential mobility spectrometer, which includes an ionization chamber for producing analyte ions from a sample to be analyzed, a filter channel for separating analyte ions of different species and a detection region for collecting analyte ions of the selected species. According to the method, the sample to be analyzed is introduced into the ionization chamber, in which analyte ions are produced, the so-obtained analyte ions are then subjected in the filter channel to a time-varying electric field. The time-varying electric field has a longitudinal field component drawing the analyte ions from the ionization chamber through the filter channel into the detection region and a transversal field component, which is the superposition of an asymmetrically oscillating transversal field causing the analyte ions to move to and fro in transversal direction and a compensation field for selecting a species of analyte ions by substantially canceling the average transversal velocity of the selected species. Analyte ions of the selected species having passed through the filter channel are collected in the detection region and a detection signal responsive to the number of analyte ions collected is generated as a function of the compensating field. The method according to the invention further proposes to make the longitudinal field component oscillate in longitudinal direction in such a way that it imparts to the analyte ions on average a non-zero longitudinal velocity in direction of the detection region while it causes them, on a shorter time scale, to move to and fro in longitudinal direction in the filter channel. As those skilled will appreciate, the oscillations of the longitudinal field component make the analyte ions change direction several times in the filter channel, which results in the length of the filter channel being virtually increased for the analyte ions. As evidenced by equations (-8-) and (-9-), this results in a better resolution of the spectrometer without that the actual geometric parameters need be changed. The method is, therefore, especially suited for application in a miniaturized DMS.

It should be noted that, in the context of the present, an "asymmetrically oscillating" electric field designates an electric field that oscillates but whose negative oscillations are not reflected copies of the positive oscillations (i.e. differ from them in shape, duration and/or amplitude when reflected in the base line).

As is always the case in differential mobility spectrometry, the analyte ions are surrounded by a carrier gas. In the method of the invention, the movement of the analyte ions along the longitudinal direction of the filter channel is predominantly caused by the action of the longitudinal component of the electric field on the analyte ions, whereas the impact of the flow of the carrier gas is negligible. In other words, the velocity communicated to the analyte ions by the longitudinal electric field component exceeds by far the velocity of the carrier gas.

According to a first aspect of the method, the longitudinal field component ($E_d$, using the above notation) is chosen asymmetrically oscillating (i.e. the duration and amplitude of the positive oscillations differ from those of the negative oscillations) and zero on average, i.e. $\int_0^T E_d(t)dt=0$, so that the average non-zero longitudinal velocity is caused by a non-linear dependence of the mobility increment of the analyte ions on the electric field. This aspect of the invention thus uses the non-linear dependence of the velocity of the analyte ions upon the electric field strength. T denotes here the period of the longitudinal electric field component.

Alternatively, the longitudinal field component may be non-zero on average i.e. $\int_0^T E_d(t)dt \neq 0$. The longitudinal field component may, for instance, comprise a sequence of pulses of alternating polarity, the polarity of the first pulse of the sequence being such that the analyte ions are drawn towards the detection region while being subjected to the first pulse. Preferably, the amplitude of the odd pulses (i.e. the $1^{st}$, $3^{rd}$, $5^{th}$, . . . pulses) of the sequence is higher than the amplitude of the even pulses (i.e. the $2^{nd}$, $4^{th}$, . . . pulses) of the sequence. Additionally or alternatively, the duration of the odd pulses of the sequence may be higher than the duration of the even pulses of the sequence. Most preferably, the duration of the first pulse of the sequence is longer than the duration of the subsequent (i.e. the $2^{nd}$, $3^{rd}$, $4^{th}$, . . . ) pulses of the sequence. The pulses are advantageously rectangular but they can also be trapezoidal, triangular or sine-shaped.

The sequence of pulses advantageously has a duration that exceeds the time of flight of the analyte ions from the ionization chamber to the detection region. Those skilled will note that the time of flight depends on the duration and amplitude of the pulses of the sequence.

The ionization chamber is preferably equipped with a pulsed ionization source, which provides the analyte ions in synchronization with the first pulse of the sequence. Thus it is ascertained that the newly formed ions are drawn into the direction of the filter channel and the detection region under the effect of the first pulse.

According to a preferred aspect of the invention, the detection signal responsive to the number of collected analyte ions is generated as a function of the compensating field and of the time of flight of the analyte ions from the ionization chamber to the detection region. Thus the time of flight may be used as an additional parameter for determining the composition of the sample to be analyzed. Those skilled will note that the concept of applying an oscillating driving field to increase the time of flight of the analyte ions could be used in an ion mobility spectrometer (which relies on the mobility $K_0$ rather than on the mobility increment to distinguish the ion species). In case of ion mobility spectrometry, the provision of separating electrodes providing an oscillating asymmetric transversal electric field is not necessary.

A differential mobility spectrometer for implementing the method described above preferably comprises an ionization chamber for producing analyte ions from a sample to be analyzed, at least one filter channel for separating analyte ions of different species, a detection region for collecting analyte ions of the selected species; and a control circuit comprising a plurality of electrodes, the control circuit being so configured and arranged as to generate a time-varying electric field in the filter channel, the time-varying electric field having a longitudinal field component drawing the analyte ions from the ionization chamber through the filter channel into the detection region and a transversal field component, the transversal field component being a superposition of an asymmetrically oscillating transversal field causing the analyte ions to move to and fro in transversal direction and a compensation field for selecting a species of analyte ions by substantially canceling the average transversal velocity of the selected species. The control circuit is further configured and arranged so as to generate a detection signal responsive to a number of analyte ions collected as a function of the compensating field and to make the longitudinal field component oscillate in longitudinal direction. These oscillations are chosen such that the longitudinal component imparts to the analyte ions on average a non-zero longitudinal velocity in direction of the detection region while on a shorter time scale it causes the analyte ions to move to and fro in longitudinal direction in the filter channel. Apart from the electrodes, the control circuit preferably comprises an application-specific integrated circuit (ASIC), a field-programmable gate array (FPGA) or a processor connected to the electrodes.

The control circuit is preferably so configured and arranged as to form the longitudinal field component from a sequence of pulses of alternating polarity, the polarity of the first pulse of the sequence being such that the analyte ions are drawn towards the detection region while being subjected to the first pulse. Advantageously, the duration of the first pulse of the sequence is longer than the duration of the subsequent pulses of the sequence.

The ionization chamber of the differential mobility spectrometer is preferably equipped with a pulsed ionization source, which is synchronized by the control circuit with the first pulse of the sequence of pulses. Such pulsed ionization source may comprise, for instance, at least one of a pulsed laser, a discharge lamp, a pulsed light emitting diode and an array of light emitting diodes.

BRIEF DESCRIPTION OF THE DRAWINGS

Further details and advantages of the present invention will be apparent from the following detailed description of several not limiting modes of carrying out the invention with reference to the attached drawings, wherein.

DESCRIPTION OF PREFERRED EMBODIMENTS

Figure 1:
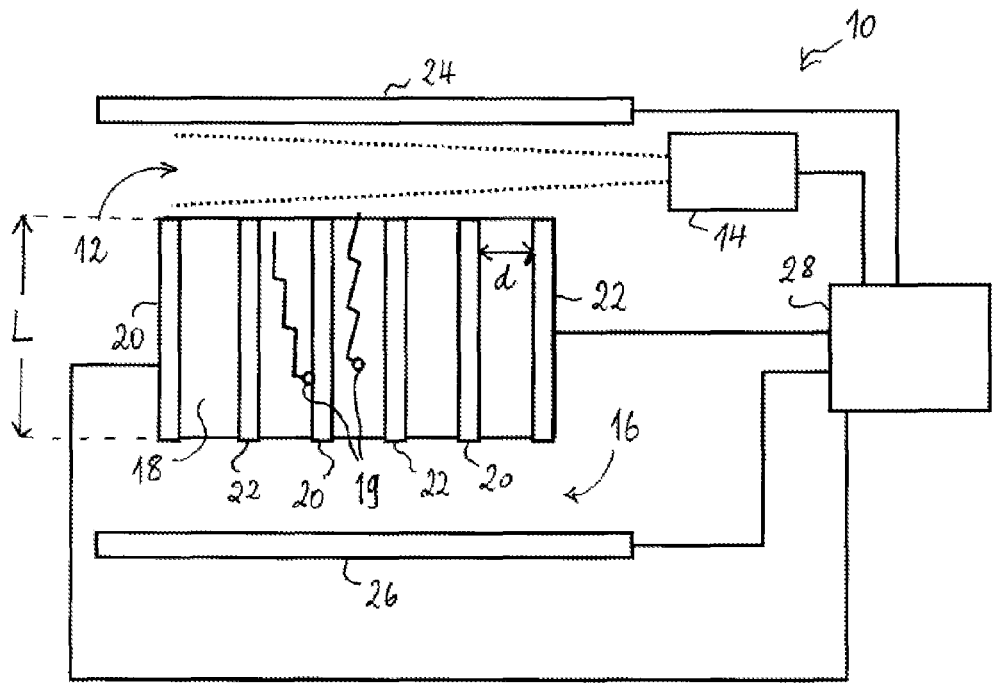
FIG. 1 is a schematic lateral view of a miniaturized differential mobility spectrometer.
Figure 2:
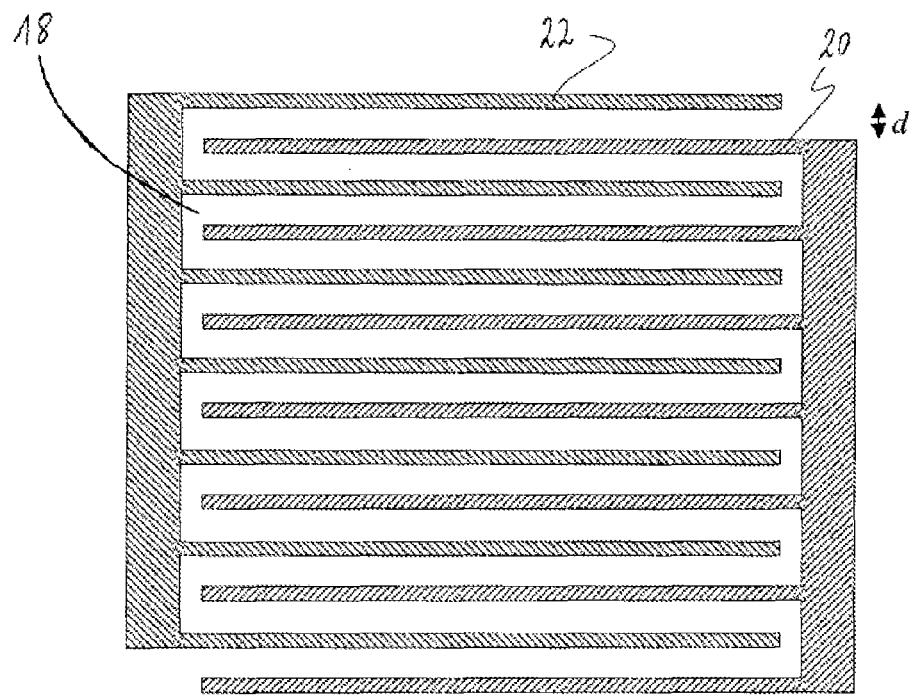
FIG. 2 is a schematic top view of separation electrodes of a differential mobility spectrometer
Figure 3:
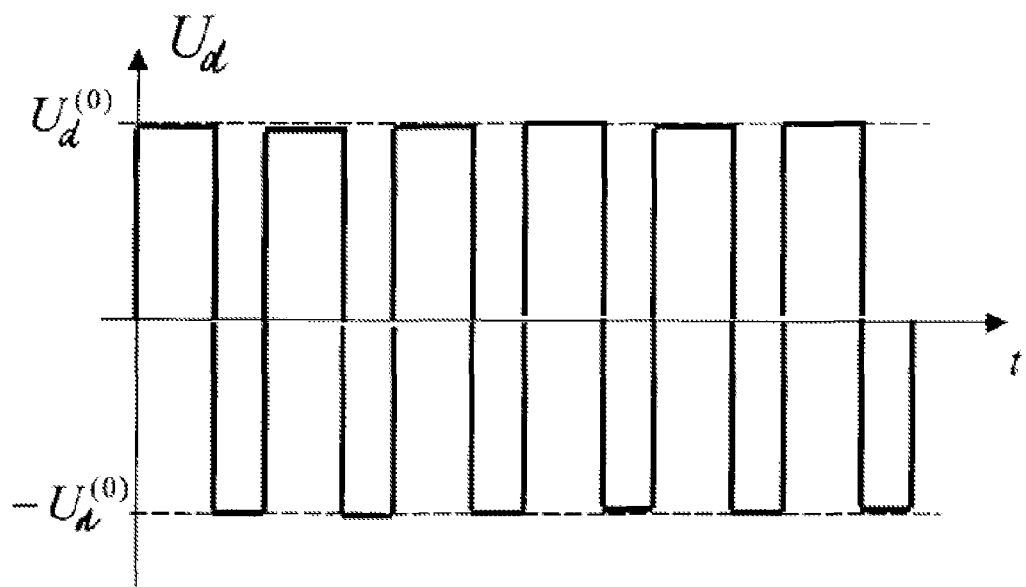
FIG. 3 is a graphical representation, as a function of time, of a voltage for generating a longitudinal electric field component according to a first example.
Figure 4:
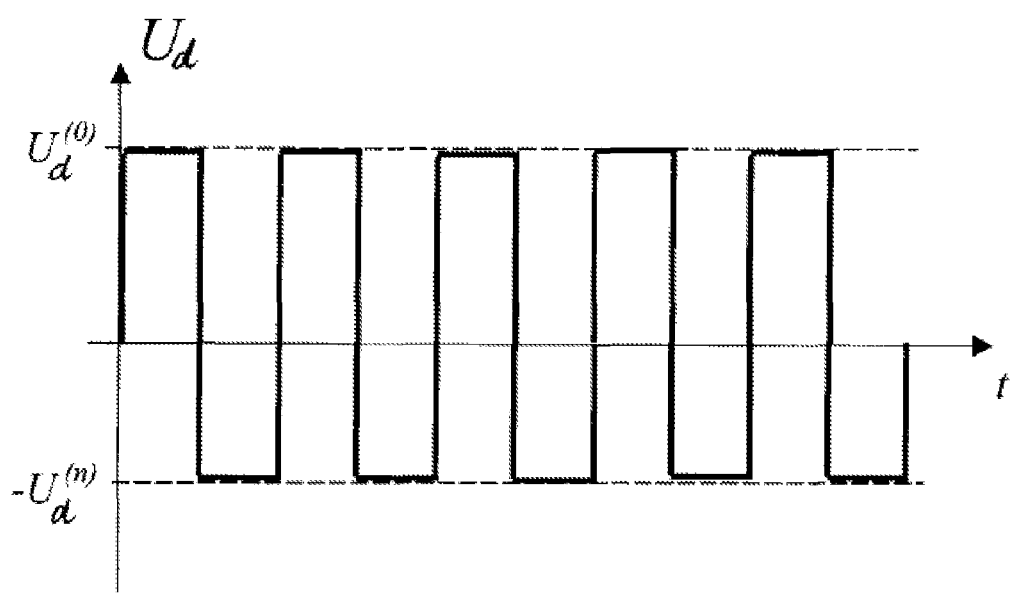
FIG. 4 is a graphical representation, as a function of time, of a voltage for generating a longitudinal electric field component according to a second example.

As illustrated in FIG. 1, a miniaturized differential mobility spectrometer 10 comprises an ionization chamber 12, in which analyte ions are produced from a sample to be analyzed by an ionization source 14 (such as, e.g. a UV laser). The ionization chamber 12 is in fluid connection with a detection region 16 via a filter channel 18. Two comb-shaped interdigitating electrodes 20 and 22 define the cross section of the filter channel 18, which is best shown in FIG. 2. The filter channel is disposed between two substantially planar deflection electrodes 24 and 26. When the spectrometer is in use, the different electric potentials are applied to electrodes 20, 22, 24 and 26, so as to produce an electric field in the region between them. In the electrode configuration as in FIG. 1, the separation electrodes 20 and 22 produce the transversal component of the electric field, whereas the deflection electrodes 24 and 26 produce the longitudinal component of the electric field. Other configurations are of course possible. When a voltage $U_d$ is applied across the deflection electrodes 24, 26 the electric field that builds up between them drives the analyte ions in longitudinal direction through the filter channel 18. The length of the filter channel 18 is denoted with "L", while its width is denoted with "d". While the analyte ions 19 are driven through the filter channel, an asymmetrically oscillating voltage is applied across the separation electrodes 20, 22, which results in an electric field, which is oriented generally transversal with respect to the electric field created by the deflection electrodes 24, 26. The superposition of these electric fields results in a time-varying electric field in the filter channel, which has a longitudinal field component and a transversal field component, the longitudinal field component drawing the analyte ions 19 from the ionization chamber 12 through the filter channel 18 into the detection region 16. The electric potentials on the electrodes 20, 22, 24, 26 are controlled by a processor 28, which also controls the ionization source 14.

As in conventional differential mobility spectrometry, the transversal field component is chosen as a superposition of an asymmetrically oscillating transversal field causing the analyte ions 19 to move to and fro in transversal direction and a compensation field for selecting a species of analyte ions by substantially canceling the average transversal velocity of the selected species. The overall motion of the analyte ions 19 follows a zigzag path between the separation electrodes. Ions, for which the residual transversal velocity remains sufficiently important, hit the lateral boundary surface of the filter channel where they recombine (i.e. lose their electric charge). Only ions 19 whose transversal velocity is sufficiently close to zero eventually enter the detection region 16, where they hit the electrode 26, which also serves as detection electrode. The processor 28 generates a detection signal responsive to the number of analyte ions 19 collected, as a function of the compensating field or voltage.

To increase the effective length of the filter channel without changing the geometry of the spectrometer, the processor drives the deflection electrodes with an alternating voltage $U_d$, in such a way that the longitudinal field component oscillates in longitudinal direction. These oscillations are chosen such that the longitudinal component imparts to the analyte ions on average (over at least one period of the oscillations of the longitudinal field component) a non-zero longitudinal velocity in direction of the detection region while on a shorter time scale (shorter than a period of the oscillations) it causes the analyte ions to move to and fro in longitudinal direction in the filter channel 18. Examples of temporal waveforms of the voltage $U_d$ are shown in FIGS. 3 to 6.

The voltage waveforms of FIGS. 3 to 6 result in a non-zero average longitudinal electric field (longitudinal electric field component)

$$\langle E_d \rangle = T^{-1} \int_0^T E_d(t) dt > 0, \qquad (-10-)$$

having the effect that, despite their back-and-forth motion, the analyte ions are subjected, on average to a net force, which draws them to the detection electrode. The advancing is, however, considerably slowed down by the oscillations of the driving field.

One can achieve such slowing down by choosing the field as a sequence of rectangular positive and negative pulses, the positive pulses having the same amplitude)$E_d^{(0)}$ as the negative pulses, while the duration $T_1$ of the positive pulses is selected higher than the duration $T_2$ of the negative ones. Such field is obtained by applying the voltage shown in FIG. 3 across the deflection electrodes. The resolution parameter r is modified by a factor κ with respect to equation (-9-) and takes the form:

$$r = \frac{d^4 N^2 U_d^{(0)}}{L^2 U_s^3 \langle f^3 \rangle \alpha_2^{(0)}} \kappa, \qquad (-11-)$$

where $\kappa = (T_1 - T_2)/(T_1 + T_2)$. By the appropriate choice of $T_2$ close to $T_1$ one may considerably decrease the resolution parameter r (and thereby increase the resolution).

In addition to giving the positive and negative pulses different duration or as an alternative thereto, the amplitude of the positive pulses $E_d^{(p)} = U_d^{(0)}/L$ may be selected somewhat larger than the amplitude of the negative pulses $E_d^{(n)} = U_d^{(n)}/L$. If the durations of the positive and the negative pulses are equal, as in FIG. 4, the resolution parameter can again be expressed by equation (-11-) where this time $\kappa = (U_d^{(0)} - U_d^{(n)})/2U_d^{(0)}$. By an appropriate choice of the amplitudes) $U_d^{(0)}$ and $U_d^{(n)}$, one decreases the parameter r.

Figure 5:
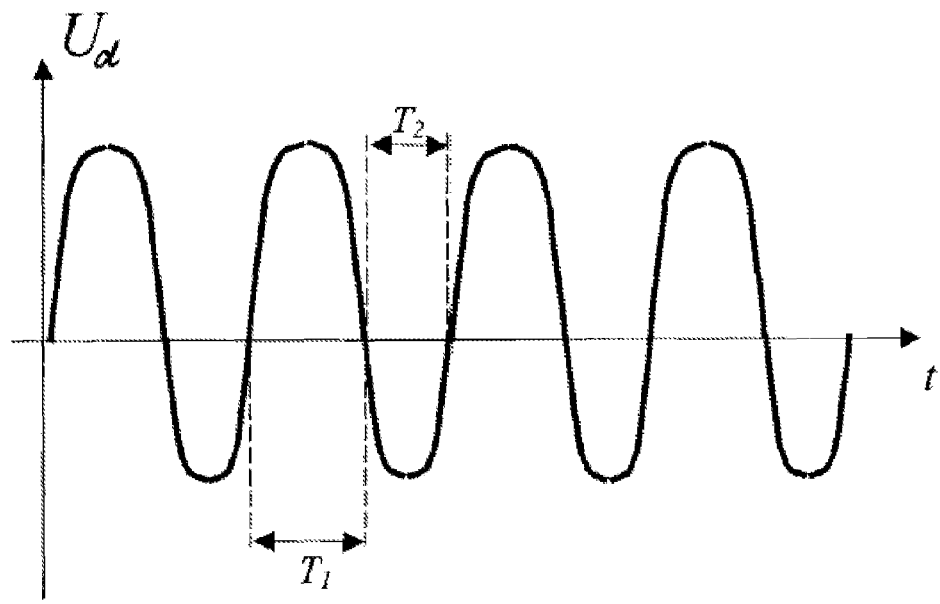
FIG. 5 is a graphical representation, as a function of time, of a voltage for generating a longitudinal electric field component according to a third example.

In the general case (neither pulse durations nor amplitudes necessarily equal and arbitrary pulse shapes), illustrated in FIG. 5, the resolution parameter still obeys equation (-11-), where the parameter)$U_d^{(0)}$ is re-defined as $$U_d^{(0)} = \{|\int_0^{T_1} U_d(t)dt| + |\int_{T_1}^{T_1+T_2} U_d(t)dt|\}/(T_1+T_2) \qquad (-12-)$$

and factor κ as $$\kappa = \frac{\int_0^{T_1} U_d(t)dt + \int_{T_1}^{T_1+T_2} U_d(t)dt}{|\int_0^{T_1} U_d(t)dt| + |\int_{T_1}^{T_1+T_2} U_d(t)dt|} \qquad (-13-)$$

If one applies the voltages of FIGS. 3 to 6 for driving the ions back and forth through in the filter, one relies preponderantly upon their mobilities $K_0$ rather than upon their mobility increments. Because typically $\alpha(E) \ll 1$ (see for example, G. A. Eiceman et al., Anal. Chem. 76, 4937 (2004); Buryakov, Talanta 61, 369 (2003) and Buryakov, ZhTF 72, 109 (2002)) and equation (10), the contribution of the mobility increment to the longitudinal motion of the ion is negligible. The mobility increment can, however, become important when the ions are so slowed down that the overall displacement during the period becomes comparable to the contribution due to the mobility increment (typically, when the motion is slowed down about by a factor of 100). Calculations for such a case are not shown.

Instead of applying an electric longitudinal field which is non-zero on average, one may choose the driving field such that $\int_0^T E_d(t)dt = 0$. In this case the large linear contributions of the electric field to the ion displacement are exactly compensated and the overall drift of the ions towards the detection chamber relies only on the mobility increment.

A preferred aspect of the invention addresses the reduction of diffusion losses. In the ionization chamber, the applied electric field draws the analyte ions from the first deflection electrode towards the filter channel and the second deflection electrode but, due to diffusion, a certain fraction of the analyte ions is carried backwards, towards the first deflection electrode. If ions reach the first deflection electrode 24 and will recombine, this decreases the amount of the analyte ions that can be filtered and makes a parasitic contribution to the current measured in the analysis circuit (i.e. between the first and the second deflection electrodes). Consider a driving electric field having the form of alternating positive and negative rectangular pulses of same amplitude but with durations $T_1$ and $T_2$, respectively. The duration $T_{in}$ of the first pulse (which is positive, i.e. oriented so that the analyte ions are drawn towards the second deflection electrode) is chosen to have a duration that exceeds the durations of the subsequent positive and negative pulses. For the diffusion contribution to be negligible, the movement of the ions caused by the electric field $K_0 U_s^{(0)}(T_{in} - T_2)/L$ during the period $T = T_{in} + T_2$ must be larger than their displacement due to diffusion during the same period, which is approximately $2\sqrt{D(T_{in} + T_2)}$, where D is the diffusion coefficient. If the ratio of the duration of the long initial forward pulse to the duration of the subsequent shorter backward pulse is denoted by x, i.e. $x = T_{in}/T_2$, preferred values for x may be derived. The following condition can therefore be established for x:

$$\frac{(1-x)}{\sqrt{1+x}} > \frac{2L}{U_d^{(0)}} \sqrt{\frac{k_B \Theta}{q K_0 T_2}} = \sqrt{z} \qquad (-14-)$$

Using the dimensionless parameter $z > 0$, which is defined as:

$$z = \frac{4L^2 k_B \Theta}{U_d^{(0)2} q K_0 T_2}, \qquad (-15-)$$

(-14-) can be transformed into the inequality $$\frac{T_{in}}{T_2} \geq \frac{1}{2}(2 + z + \sqrt{z^2 + 8z}). \qquad (-16-)$$

For example, with the parameter values L=200 μm, $K_0 \approx 1$ cm²/V×s, $T_2 = 1 \times 10^{-8}$ s, an ion charge of $q = 1.6 \times 10^{-19}$ C, one finds, at room temperature $k_B \Theta \approx 4.2 \times 10^{-21}$ J, different ratios x for a given driving voltage. $U_d = 50$ V yields $T_{in}/T_2 \approx 9.33$, $U_d = 100$ V yields $T_{in}/T_2 \approx 3.86$ while $U_d = 150$ V yields $T_{in}/T_2 \approx 2.65$. It can be derived from (-15-) that $T_{in}/T_2$ appears to be sensitive to the length L of the filter channel. For example, at the voltage $U_d = 100$ V, one finds for the thicknesses of 200, 300 and 400 μm the ratios $T_{in}/T_2$ of 3.86, 6.23 and 9.33, respectively.

The pulses of the longitudinal electric field component are preferably organized in groups (referred to as sequences or "wave packets"), each such group containing one initial long positive pulse (of duration $T_{in}$), n short positive pulses (of duration $T_1<T_{in}$) and n negative pulses (of duration $T_2$, with $T_2<T_1$) so that the overall duration of each group exceeds the time of flight of the analyte ions from the ionization chamber to the detection region, i.e. $T_{in}+n(T_1+T_2)>T_f$. In preferred embodiments of the invention, the duration of the initial pulse amounts to between 1.5 to 20 times (more preferably: between 2 and 10 times) the duration of the (even) backward pulse. The duration of the initial pulse is preferably also chosen between 1.25 and 10 times (more preferably: between 1.5 and 5 times) the duration of the other odd pulses. It should be noted that the period of the separating field, denoted herein as $T_s$, and the period T of the longitudinal electric field (the driving field) are independent from one another. One has preferably $T/T_s \sim 10$ and more preferably $T/T_s \sim 100$, but other ratios may be chosen as well.

Figure 6:
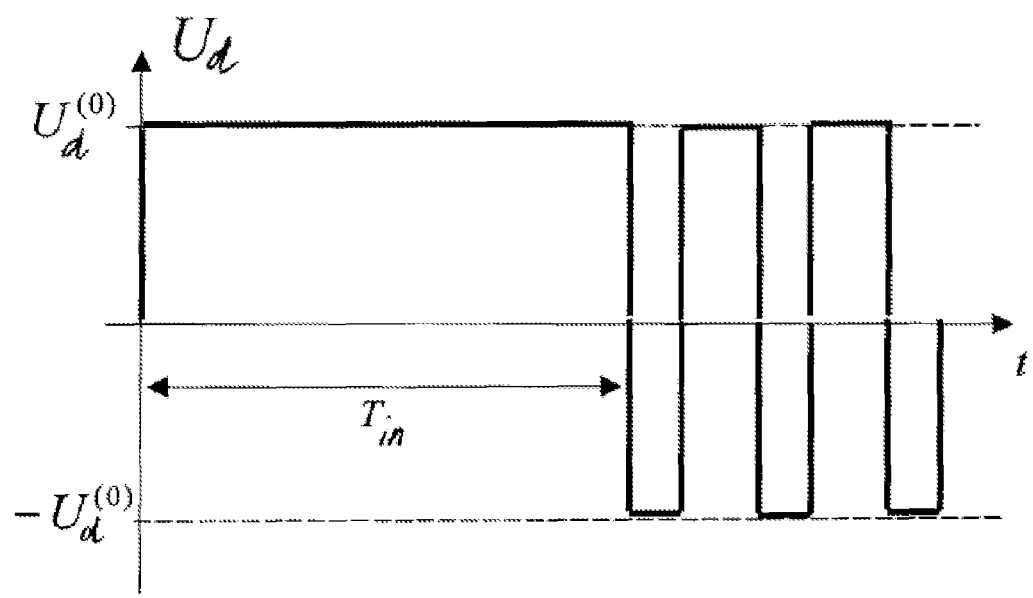
FIG. 6 is a graphical representation, as a function of time, of a voltage for generating a longitudinal electric field component according to a fourth example.

FIG. 6 shows an example of a waveform of the voltage applied across the first and second deflection electrodes corresponding to such longitudinal electric field component.

Those skilled will readily recognize that the pulses of such a group or sequence may have any shape and amplitude. Of course, the initial pulse is preferably not so long that the selected analyte ions reach the detection electrode within its duration.

According to yet another preferred aspect of the invention, the differential mobility spectrometer comprises a pulsed ionization source, such as e.g. the pulsed UV laser of FIG. 1, a discharge lamp, a UV LED, an array of UV LEDs, or an X-ray source. The ionization source preferably emits pulses of UV light that are synchronized with the first pulse of each group (or sequence or wave packet). Preferably, the duration of the first pulse is at least as long as the duration of the pulse of ionizing radiation. Indeed, if analyte ions are produced after the end of the initial (possibly long) pulse, these will be at least partially brought to the first deflection electrode 24, where they can recombine. Since this would lead to loss of efficiency of the device, it is preferred that no ionization occurs as long when there is no electric field that draws the ions formed into the filter channel and towards the detection region.

To increase the efficiency of the spectrometer, the ionization pulses are preferably synchronized with the pulses of the longitudinal electric field component in such a way that the beginning of each ionization pulse coincides with the beginning of the initial (long) pulse of the longitudinal field component. The duration of the ionization pulse (denoted $T_i$) is chosen so that $T_i<T_{in}$ and preferably so that $T_i \ll T_{in}$. In practice, it is often the repetition rate of the ionization source that limits the repetition rate of the wave packets.

In order to provide a successful single-photon ionization of organic volatile compounds the UV source must provide photons carrying at least the energy of 10 eV. This photon energy is provided, for instance, by a krypton discharge lamp. However, a pulsed laser emitting photons exceeding 10 eV would be more preferred.

Figure 7:
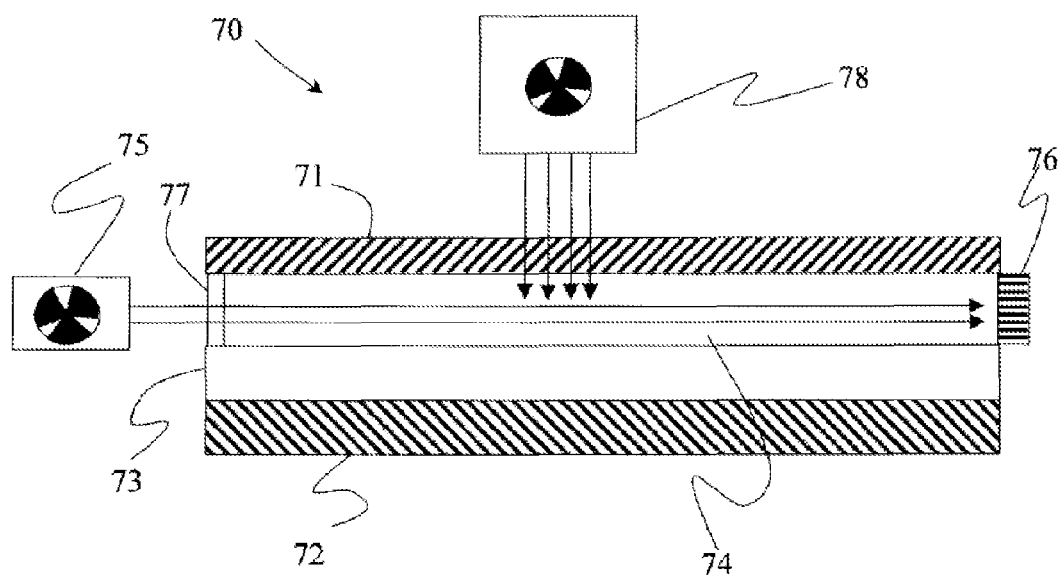
FIG. 7 shows a schematic lateral view of a miniaturized differential mobility spectrometer in a further variant.

The differential mobility spectrometer 70 according to the variant of FIG. 7 comprises an ionization chamber 74, a first deflection electrode 71, a separation chamber 73 comprising one or more filter channels (not shown) and a detection region on the surface of the second deflection electrode 72. The ionization chamber is in fluid connection with the detection region 16 via the one or more filter channels. The electrode configuration in the variant of FIG. 7 is essentially the same as in FIG. 1 and will not be discussed again to avoid unnecessary repetition. The ionizing light originating from a suitable light source 75, such as e.g. a UV laser, is delivered to the ionization chamber through a UV-transparent window 77 in the wall of the ionization chamber 74. Most advantageously, the window 77 is semi-reflecting while the opposite wall of the ionization chamber is a mirror 86 parallel to the window. This will have the benefit of multiple reflections of the UV light within the ionization chamber 74, which increases the production of ions. The light of a second pulsed ionization source 78 enters into the ionization chamber 74 through the first deflection electrode 71, which is made semi-transparent for that light. The first deflection electrode 71 may e.g. be made of a UV-transparent glass with having one surface coated with a thin gold layer.

Figure 8:
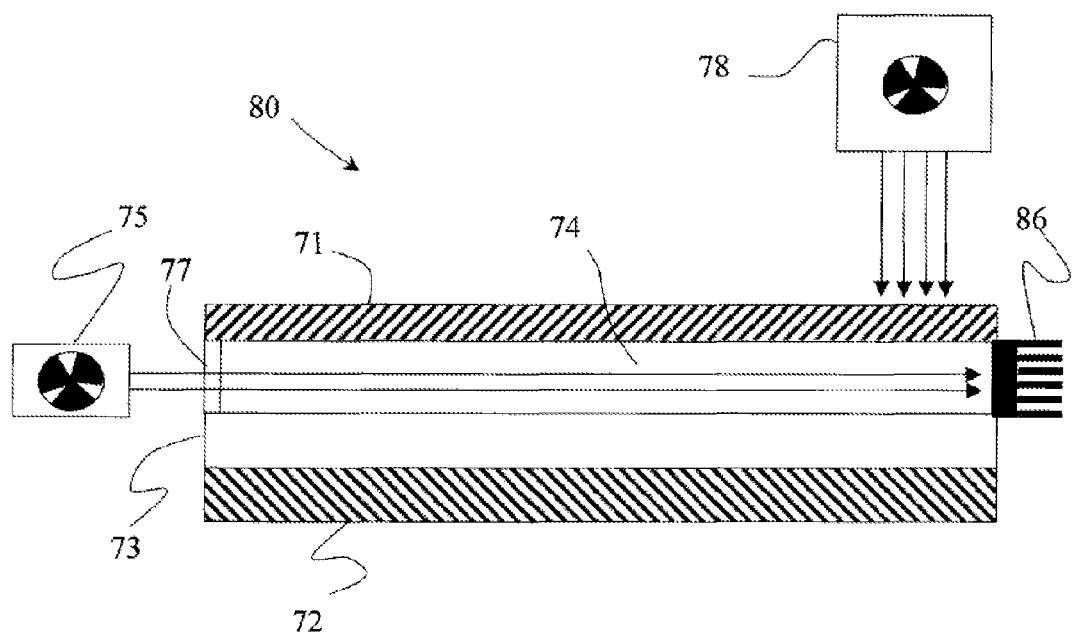
FIG. 8 shows a schematic lateral view of a miniaturized differential mobility spectrometer in yet another a further variant.

A slightly different variant of a miniaturized differential mobility spectrometer 80 is shown in FIG. 8. The elements already discussed with respect to FIG. 7 have been given the same reference numerals. In the spectrometer 80, the wall opposite the semi-transparent window 77 comprises a substrate, which is in thermoconducting connection with a radiator 86, which cools the substrate. The pulsed light source 75 is arranged in such a way that its ionizing light beam irradiates the substrate. Before the light pulses hit the surface of the substrate, the latter is cold and adsorbs the analytes from the gas. When a light pulse irradiates the substrate, the thin film of adsorbed analytes and the underlying substrate heat up, causing the adsorbed analyte molecules to evaporate and form a dense cloud over the substrate. The analyte molecules are ionized by the light beams from the ionization source 75 and the optional ionization source 78. Since also in this variant the ionization sources are synchronized with the first longitudinal electric field pulse of each wave packet, the ions are drawn into the one or more filter channels, where separation is carried out. Between the light pulses, the substrate is cooled by the radiator 86, so that again analyte molecules are adsorbed and the above steps are repeated cyclically. The substrate is preferably made of a metal with high temperature conductivity, such as, e.g. tungsten, silver, copper, gold, etc., preferably having a high melting point. The repetition rate of the light pulses should be chosen such that the substrate is sufficiently cooled between the pulses. If X is the thickness of the substrate (from the surface on which the molecules condensate to the radiator) and $\chi$ is its thermal diffusivity, the repetition frequency of the pulses should obey the inequality $\omega \ll \chi/X^2$.

Those skilled will note that instead of relying on single-photon ionization, one may also use a two-photon ionization. However, this requires that the analyte molecules subjected to the ionization have an intermediate energy level with a relatively long lifetime. In two-photon ionization, the molecule is excited from its ground state to this level by a first photon and is then further excited to the ionized state by a second photon. Benzene rings possess such an intermediate level at approximately 5 eV while their ionization energy amounts to about 10 eV. Therefore, most molecules with aromatic groups may be ionized by the two-photon mechanism. Since most of materials of a potential interest include aromatic components, optical, pulsed, two-photon ionization synchronized with the wave packet is a preferred variant of the method according to the present invention.

The two-photon ionization can be performed by a pulsed UV laser providing photons with an energy of at least 5 eV. The laser pulse duration T is preferably chosen equal to or smaller than the typical lifetime of the intermediate energy level. For example, it can be chosen below 200 ns, more preferably below 100 ns, and even more preferably below 30 ns.

The intensity of the light source is preferably high. However, if the surface-assisted ionization is used, too high intensity will cause complete decomposition of organic volatile compounds. For this reason, the intensity of the light ranges preferably from $10^2$ to $10^8$ W/cm$^2$ and more preferably from $10^4$ to $10^6$ W/cm$^2$.

Those skilled will appreciate that all spectrometer configurations with the adsorbing substrate described above are compatible with both single-photon and two-photon ionization. In all configurations, it is highly preferred that the ionizing light pulses are synchronized with the longitudinal electric field component.

As has been briefly discussed hereinabove, the time of flight of the analyte ions from the ionization chamber to the detection region may be used as an additional information to determine the composition of the sample to be analyzed. It has been mentioned two different ion species with different mobilities $K_0^{(1)}$ and $K_0^{(2)}$ but the products close enough to one another $K_0^{(1)}\alpha^{(1)} \approx K_0^{(2)}\alpha^{(2)}$ may be indistinguishable by the DMS filter. Due to the difference in their mobilities $K_0^{(1)}$ and $K_0^{(2)}$, such species can still be separated using their time of flight. We consider this in more detail for the example of an asymmetric longitudinal electric field with rectangular positive and negative pulses of same amplitude but in which the duration of the positive pulses $T_1$ exceeds the duration $T_2$ of the negative pulses. The difference in the times of flights of the ions is $$\Delta T_f = \frac{L^2 \Delta K_0}{\kappa U_d K_0^{(1)} K_0^{(2)}}, \quad (-17-)$$

where $\kappa = (T_1 - T_2)/(T_1 + T_2)$ ($\kappa$ is herein referred to as the "retardation coefficient") and $\Delta K_0 = |K_0^{(1)} - K_0^{(2)}|$. By an appropriate choice of $T_1$ close to $T_2$ one may increase this difference (e.g. by a factor of 10 with respect to the case where there is only a constant driving field ($T_2=0$). The peaks of electric current corresponding to these ion species and detected by the control circuit are therefore separated in time. The detection signal generated by the control circuit is a function of the compensating field and of the time of flight of the analyte ions. In this way, the discrimination of the different ions species relies on two parameters instead of one, which increases the sensitivity of the spectrometer and reduces the number of analyte species that cannot be separated in the spectrometer. Indeed, the probability that the mobilities $K_0^{(1)}$, $K_0^{(2)}$ of any two species and their products $K_0^{(1)}\alpha^{(1)}$, $K_0^{(1)}\alpha^{(2)}$ coincide is an improbable event.

Ion mobility values are typically of the order of 1 cm$^2$/(V×s): $K_0^{(1)} \approx K_0^{(2)} \approx 1$ cm$^2$/(V×s). For example, the mobility of ionized benzene is 2.22 cm$^2$/(V×s), that of ethylbenzene 1.94 cm$^2$/(V×s), that of dimethylbenzene 1.93 cm$^2$/(V×s) (Borsdorf, H. *Analytica Chimica Acta* 575, 76 (2006)), that of chlorobenzene 1.79 cm$^2$/(V×s), while that of chlorotoulene is 1.69 cm$^2$/(V×s) (Borsdorf, H. & Eiceman, G. A. *Applied Spectroscopy Reviews* 41, 323 (2006)). Thus, one can expect differences in the mobilities in the interval $\Delta K_0 \approx 0.01$ to 1 cm$^2$/(V×s). Consider a device with filter length L=200 μm, a voltage $U_d$=40 V across the deflection electrodes and assume that the retarding coefficient is $\kappa$=0.1. Expression (-17-) yields that the times of flight spread in the interval $\Delta T_f \approx 10^{-7}$ to $10^{-5}$ s.

Those skilled in the art will recognize that the discrimination between different analyte species using the time of flight information may be carried out without any filtering with respect to the mobility increment. A device operating in this way is then a time-of-flight ion filter, such as the Ion Mobility Spectrometer. In this case, the back and forth motion of the analyte ions imposed by the oscillating longitudinal electric field component has the effect of increasing of the effective time of flight in the device and thus increases its resolution. This is useful, in particular, for miniaturized time-of-flight spectrometers (micro-TOF spectrometers).

The invention claimed is:

1. A method of operating a differential mobility spectrometer, said differential mobility spectrometer including an ionization chamber, a filter channel and a detection region, said method comprising:
   introducing a sample to be analyzed into said ionization chamber so as to produce analyte ions;
   subjecting said analyte ions in said filter channel to a time-varying electric field, wherein said time-varying electric field has a longitudinal field component drawing said analyte ions from the ionization chamber through said filter channel into said detection region and a transversal field component, said transversal field component being a superposition of an asymmetrically oscillating transversal field causing said analyte ions to move to and fro in transversal direction and a compensation field for selecting a species of analyte ions by substantially canceling an average transversal velocity of said selected species;
   collecting analyte ions of said selected species in said detection region; and
   generating a detection signal responsive to a number of analyte ions collected as a function of said compensating field;
   wherein said longitudinal field component is non-zero on average and comprises a sequence of pulses of alternating polarity, a polarity of a first pulse of said sequence being such that the analyte ions are drawn towards the detection region while being subjected to said first pulse, and
   wherein said longitudinal field component oscillates in longitudinal direction so that said analyte ions are imparted on average a non-zero longitudinal velocity in direction of said detection region while on a time scale shorter than a time required for said analyte ions to travel from said ionization chamber to said detection region they are caused to move to and fro in longitudinal direction while they are subjected to said asymmetrically oscillating transversal field in said filter channel, said longitudinal field component oscillating in longitudinal direction resulting for said analyte ions in a virtual increase in length of said filter channel.

2. The method according to claim 1, wherein an amplitude of the odd pulses of said sequence is higher than an amplitude of the even pulses of said sequence.

3. The method according to claim 1, wherein a duration of the odd pulses of said sequence is higher than a duration of the even pulses of said sequence.

4. The method according to claim 1, wherein a duration of the first pulse of said sequence is longer than a duration of subsequent pulses of said sequence.

5. The method according to claim 1, wherein said sequence has a duration that exceeds a time of flight of said analyte ions from said ionization chamber to said detection region.

6. The method according to claim 1, wherein said ionization chamber is equipped with a pulsed ionization source, and wherein said analyte ions are provided by said pulsed ionization source in synchronization with a first pulse of said sequence.

7. The method as claimed in claim 1, wherein said longitudinal field component comprises sequence of pulses organized in groups, each group containing one initial long positive pulse, a number of short positive pulses and the same number of short negative pulses, so that the overall duration of each group exceeds the time required for said analyte ions to travel from said ionization chamber to said detection region.

8. The method as claimed in claim as claimed in claim 7, wherein said pulses are at least one of rectangular, trapezoidal, triangular and sine-shaped.

9. A differential mobility spectrometer, comprising
an ionization chamber to produce analyte ions from a sample to be analyzed,
a filter channel to separate analyte ions of different species;
a detection region to collect analyte ions of said selected species; and
a control circuit comprising a plurality of electrodes, said control circuit being so configured and arranged as to
generate a time-varying electric field in said filter channel, said time-varying electric field having a longitudinal field component drawing said analyte ions from the ionization chamber through said filter channel into said detection region and a transversal field component, said transversal field component being a superposition of an asymmetrically oscillating transversal field causing said analyte ions to move to and fro in transversal direction and a compensation field for selecting a species of analyte ions by substantially canceling an average transversal velocity of said selected species; and
generate a detection signal responsive to a number of analyte ions collected as a function of said compensating field;
wherein said control circuit is further so configured and arranged as to form said longitudinal field component from a sequence of pulses of alternating polarity, a polarity of a first pulse of said sequence being such that the analyte ions are drawn towards the detection region while being subjected to said first pulse thereby making said longitudinal field component oscillate in longitudinal direction in such a way that said longitudinal field component imparts to said analyte ions on average a non-zero longitudinal velocity in direction of said detection region while on a time scale shorter than a time required for said analyte ions to travel from said ionization chamber to said detection region it causes said analyte ions to move to and fro in longitudinal direction while they are subjected to said asymmetrically oscillating transversal field in said filter channel, said longitudinal field component oscillating in longitudinal direction resulting for said analyte ions in a virtual increase in length of said filter channel.

10. The differential mobility spectrometer according to claim 9, wherein a duration of a first pulse of said sequence is longer than a duration of subsequent pulses of said sequence.

11. The differential mobility spectrometer according to claim 9, wherein said ionization chamber is equipped with a pulsed ionization source, said pulsed ionization source being synchronized by said control circuit with a first pulse of said sequence of pulses.

12. The differential mobility spectrometer according to claim 11, wherein said pulsed ionization source comprises at least one of a pulsed laser, a discharge lamp, a pulsed light emitting diode and an array of light emitting diodes.

13. The differential mobility spectrometer as claimed in claim 9, wherein said longitudinal field component comprises sequence of pulses organized in groups, each group containing one initial long positive pulse, a number of short positive pulses and the same number of short negative pulses, so that the overall duration of each group exceeds the time required for said analyte ions to travel from said ionization chamber to said detection region.

14. The differential mobility spectrometer as claimed in claim 13, wherein said pulses are at least one of rectangular, trapezoidal, triangular and sine-shaped.

15. A differential mobility spectrometer, comprising an ionization chamber to produce analyte ions from a sample to be analyzed,
a filter channel to separate analyte ions of different species;
a detection region to collect analyte ions of said selected species; and
a control circuit comprising a plurality of electrodes, said control circuit being so configured and arranged as to
generate a time-varying electric field in said filter channel, said time-varying electric field having a longitudinal field component drawing said analyte ions from the ionization chamber through said filter channel into said detection region and a transversal field component, said transversal field component comprising a superposition of an asymmetrically oscillating transversal field causing said analyte ions to move to and fro in transversal direction and a compensation field for selecting a species of analyte ions by substantially canceling an average transversal velocity of said selected species; and
generate a detection signal responsive to a number of analyte ions collected as a function of said compensating field;
wherein said control circuit is further so configured and arranged as to form said longitudinal field component from a sequence of pulses of alternating polarity, a polarity of a first pulse of said sequence being such that the analyte ions are drawn towards the detection region while being subjected to said first pulse, thereby making said longitudinal field component oscillate in longitudinal direction in such a way that said longitudinal field component imparts to said analyte ions on a first time scale a non-zero longitudinal velocity in direction of said detection region while on a second time scale shorter than said first time scale it causes said analyte ions to move to and fro in longitudinal direction in said filter channel, said longitudinal field component oscillating in longitudinal direction resulting for said analyte ions in a virtual increase in length of said filter channel.

16. The differential mobility spectrometer according to claim 15, wherein a duration of a first pulse of said sequence is longer than a duration of subsequent pulses of said sequence.

17. The differential mobility spectrometer according to claim 15, wherein said ionization chamber is equipped with a pulsed ionization source, said pulsed ionization source being synchronized by said control circuit with the first pulse of said sequence of pulses.

18. The differential mobility spectrometer according to claim 17, wherein said pulsed ionization source comprises at least one of a pulsed laser, a discharge lamp, a pulsed light emitting diode and an array of light emitting diodes.

19. The differential mobility spectrometer as claimed in claim 15, wherein said longitudinal field component comprises sequence of pulses organized in groups, each group containing one initial long positive pulse, a number of short positive pulses and the same number of short negative pulses, so that the overall duration of each group exceeds a time required for said analyte ions to travel from said ionization chamber to said detection region.

20. The differential mobility spectrometer as claimed in claim 19, wherein said pulses are at least one of rectangular, trapezoidal, triangular and sine-shaped.

* * * * *